United States Patent
Stetler-Stevenson et al.

[11] Patent Number: 5,869,277
[45] Date of Patent: Feb. 9, 1999

[54] METHOD FOR MEASURING TYPE IV COLLAGENASE

[76] Inventors: William G. Stetler-Stevenson, 11227 White Barn Ct., Gaithersburg, Md. 20879; Lance Liotta, 9027 Mistwood Dr., Potomac, Md. 20854

[21] Appl. No.: 789,652

[22] Filed: Nov. 8, 1991

Related U.S. Application Data

[62] Division of Ser. No. 470,603, Jan. 26, 1990, abandoned.

[51] Int. Cl.$^6$ .............................. C12Q 1/28; C12Q 1/37; G01N 33/53
[52] U.S. Cl. .................................. 435/28; 435/7.1; 435/4; 435/23; 435/18; 435/7.94; 435/7.93; 435/7.92; 530/356; 530/354
[58] Field of Search ........................ 435/29, 7.93, 7.92, 435/7, 28, 7.1, 4, 23, 18, 7.94; 436/518; 530/356, 354

[56] References Cited

U.S. PATENT DOCUMENTS

| | | | |
|---|---|---|---|
| 4,446,232 | 5/1984 | Liotta ...................................... | 435/7.93 |
| 4,677,058 | 6/1987 | Tryggvason et al. ................... | 435/7.92 |
| 4,804,625 | 2/1989 | Morrison et al. ....................... | 435/7.93 |

OTHER PUBLICATIONS

Lydia Woods Schindler, "Understanding the Immune System," NIH Pub. No. 92–529, p. 36 (U.S. Dep't of Health & Human Servs. Oct. 1991).

Robertson et al; A sensitive Microplate Assay for Detection of Proteolytic Enzymes Using Radiolabeled Gelatin, Analytical Biochem 172, pp. 284–287 (1988). Month not available.

*Primary Examiner*—Louise N. Leary
*Attorney, Agent, or Firm*—Susan S. Rucker

[57] ABSTRACT

The present invention relates to the development of a modified substrate capture immunoassay useful in the detection of a neutral metalloproteinase enzyme, type IV collagenase. Capture and immobilization of this enzyme can be achieved by coating the microtiter plate with gelatin, an alternative substrate for this enzyme. The captured enzyme can then be detected by affinity purified rabbit anti-type IV collagenase antibodies prepared against synthetic peptides from the amino terminus of the enzyme. Soluble type IV collagenase can readily be detected in samples known to contain this enzyme. Using purified enzyme this assay method can detect less than 50 ng of latent type IV collagenase. Using EDTA, an inhibitor of this metalloproteinase, gelatin binding can be shown to be independent of catalytic activity.

2 Claims, 5 Drawing Sheets

AMINO TERMINUS (PEPTIDE 1–17)

```
1         10
|         |
APSPIIKFPGDVAPKTD      TYPE IV PROCOLLAGENASE
       FPATLETQEQ      INTERSTITIAL PROCOLLAGENASE
     YPLD AARGEDT      PROSTROMELYSIN
```

INTERNAL PEPTIDE (Pep472–490)

```
472    480       490
|      |         |
DKPMGPLLVATFWPELPEK    TYPE IV PROCOLLAGENASE
PEVELNFISV-FWPQLPNG    INTERSTITIAL PROCOLLAGENASE
LEPELHLISS-FWPSLPSG    PROSTROMELYSIN
```

METHOD FOR MEASURING TYPE IV COLLAGENASE

This is a division of application Ser. No. 07/470,603 filed Jan. 26, 1990, abandoned.

SUMMARY OF THE INVENTION

This invention provides an improved method for quantitation of type IV collagenase, a proteolytic enzyme involved in the invasion process and associated with the metastasis of tumor cells.

Solid phase immunoassays, e.g.,enzyme-linked immunosorbent assay (ELISA), have been widely used in immunologic studies since their first description in 1971 (Engvall and Perlman, 1971; Van Weeman and Schurrs, 1971). Various types of assay procedures have been described all of which require the immobilization of antigen or antibody. Usually, the strong interaction of peptide or protein antigens and antibodies with several kinds of plastic, such as polystyrene or polyvinyl chloride, forms the basis for fixation to the solid phase (Leininger et. al., 1966; Catt and Treager, 1967). Coating in the ELISA is usually achieved by contact of the diluted antigen or antibody with these plastic surfaces, commonly by using a sodium carbonate buffer of pH 9–10 (Hudson and Hay, 1980). A natural protease substrate as a solid phase for capturing a neutral metalloproteinase enzyme capable of degrading gelatin and type IV collagenis is now disclosed. The method is a modification of a standard capture assay technique in which a metalloprotease substrate is used to capture the enzyme of interest.

In this modified sandwich assay (FIG. 1), gelatin is bound to a solid substrate and the plate may then be washed. Varying amounts of a putative source of a soluble type IV collagenase of interest are introduced. The plate is then washed and the amount of bound enzyme is determined using affinity purified, rabbit anti-peptide antibodies against type IV collagenase followed by goat anti-rabbit-peroxidase conjugate. This method is specific for type IV collagenase in that it does not show cross reactivity with other matrix metalloproteinases, such as interstitial collagenase or stromelysin.

Type IV collagenase has been closely linked to the metastatic phenotype in humans and animal tumor models. The detection of this enzyme in a solid phase immunoassay would be of value in screening patients for metastatic disease. The method described can be used in detecting the presence of type IV collagenase in human serum or urine samples. The diagnostic methods disclosed can be used to evaluate the status of high risk individuals for particular malignancies to which they are believed to be susceptible. Furthermore, the method taught herein can be used to monitor the condition of patients who have been treated for malignancies or who are undergoing therapy.

BACKGROUND OF THE INVENTION

Degradation of basement membranes is a crucial step in tumor invasion and metastasis (Liotta, 1986). Type IV collagenase is an important proteolytic enzyme involved in the invasion process. This enzyme has been closely linked to the metastatic potential of tumors in human and murine tumor models (Liotta et. al., 1980; Bonfil et al., 1989) and is augmented following the genetic induction of the metastatic phenotype (Muschel et. al., 1985; Garbisa et. al., 1987).

The rapid detection and quantitation of this enzyme in biologic substrates would enable further exploration of the correlation between enzyme levels of type IV collagenase and the biologic behavior of tumor tissues.

FIGURE LEGENDS

FIG. 1

Type IV Collagenase Substrate Capture Immunoassay. A diagrammatic representation of the steps involved in the assay. First the ELISA plate is coated with gelatin to form the capture phase. The sample is then introduced into the well and binding of the enzyme to the gelatin occurs. The well is then washed to remove unbound material and affinity purified anti-type IV collagenase peptide antibodies are introduced. Detection of the antigen antibody complex is achieved using goat anti-rabbit antibody-horseradish peroxidase conjugate.

FIG. 2

Amino acid sequences of the amino terminal (peptide 1–17) and internal domain (peptide 472–490) peptides of type IV procollagenase used to generate anti-peptide antibodies. These sequences are compared with the corresponding regions of interstitial procollagenase and prostromelysin. The sequences for type IV procollagenase (top line) show little homology with either interstitial procollagenase (middle line) or prostromelysin (bottom line).

FIG. 3

Characterization of anti-type IV collagenase peptide antibodies. A. Characterization of affinity purified antibody A47214 490. ELISA plate wells were coated with the indicated amounts of peptide 472–490-BSA conjugate. Antibody dilutions were tested using a direct ELISA assay. B. Characterization of affinity purified antibody A1–17. ELISA plate wells were coated with the indicated amounts of peptide 1–17-BSA conjugate. Antibody dilutions were tested using a direct ELISA assay. C. Competition ELISA assay. ELISA plates were coated with 20 ng of peptide-BSA conjugate per well. The ability of unconjugated peptides to compete for antibody binding were tested by preincubating the appropriate antibody with the indicated amounts of free peptide. Both peptide 1–17 and peptide 472–490 showed complete reversal indicating that these affinity purified antibodies were monospecific. Peptide 1–17 showed no ability to compete for antibody A472–490 binding. Likewise peptide 472–490 showed no competition for antibody A1–17 binding.

FIG. 4

Effect of Calcium ion and Temperature on Gelatin Capture Immunoassay. A. Calcium ion effects. Inclusion of 5 mM calcium ion in the diluent and wash buffers resulted in a significant loss of color development when using conditioned media as a source of antigen. Inclusion of low concentrations of EDTA (10 $\mu$M) improved antigen detection only slightly. Higher concentrations of EDTA did not further improve antigen detection. B. Temperature Effects. Color development was enhanced when the experiments were performed at 4° C. as compared to results obtained when experiments were performed at 25° C.

FIG. 5

Sensitivity of the Substrate Capture Immunoassay. Serial two-fold dilutions of purified type IV collagenase were performed using the substrate capture immunoassay technique. The assay was capable of detecting less than 50 ng per well (i.e. 0.3 ng/$\mu$L).

FIG. 6

Assessment of reproducibility. Serial two-fold dilutions of conditioned media were performed in the substrate capture immunoassay procedure. Identical results were obtained for conditioned media samples when compared by assays performed on the same plate (Assay #1 and Assay #2) or on different days (Assay #3).

FIG. 7

Assessment of specificity. Serial two-fold dilutions of purified enzyme samples were performed in the substrate capture immunoassay procedure. Purified human synovial collagenase (☐) and purified human stromelysin (☐) showed no reactivity in this assay even at high concentrations tested. Purified human type IV collagenase (♦) showed concentration dependent reactivity.

DETAILED DESCRIPTION OF THE INVENTION

Figures 1, 2:
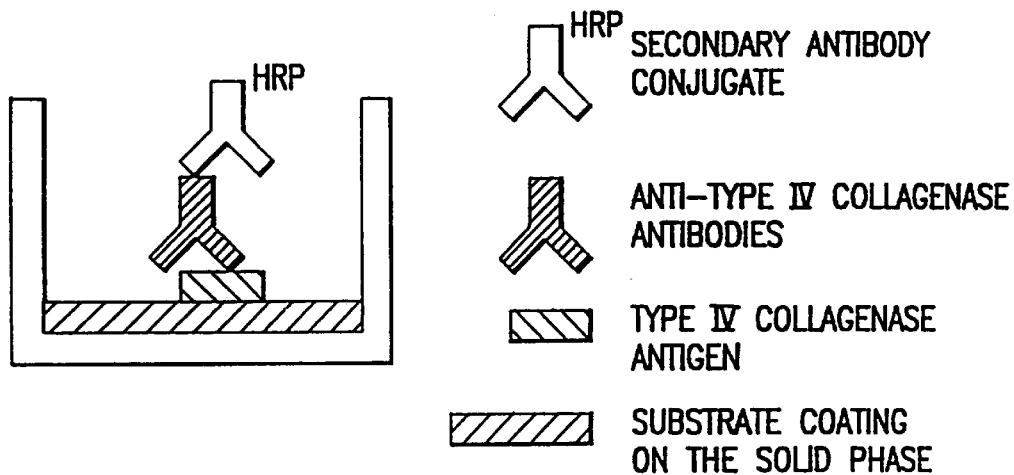

It is desirable, in evaluating the status and progress of patients suffering from malignancies to measure the collagenase in body fluids. The instant invention provides a quantitative measure of the collagenase.

The invention comprises the steps of exposing solid substrates to gelatin to provide substrates with gelatin bound thereto. The substrates are then exposed to varying amounts of the collagenase of interest or to test samples believed to contain that collagenase. Antibodies against the collagenase of interest are then applied to the substrates. After the antibodies have been allowed to bind to the collagenases the substrates are washed. The substrates are then exposed to an antibody-peroxidase conjugate which will bind to the first antibody under conditions which enhance binding of the antibody-peroxidase conjugate to the antibody which is bound to the collagenase of interest. The substrates are again washed and a peroxidase color development reagent introduced. The substrates having bound thereto known amounts of collagenase are compared with the substrates exposed to the test samples The antibodies used in the method of the invention can be either monoclonal or polyclonal in nature. The choice of antibody is limited only by the requirement that it recognize the collagenase of interest in the native conformation while bound to gelatin. The peroxidase-antibody conjugate can also be either polyclonal or monoclonal but must be directed against the anti-collagenase antibody. Alternatively the first antibody could be coupled directly to peroxidase or other detection system, such as alkaline phosphatase or radioactive iodine, thus eliminating the need for a second antibody.

While other ELISA test are known the use of the substrates having gelatin bound thereto, as described herein, provides improved sensitivity and specificity of the test.

MATERIALS AND METHODS

Materials: Immulon TM 2 flat bottom 96 well microtitration plates were obtained from Dynatech Laboratories, Inc. The ELISAmate® kit system (Microwell ELISAmate ® for Peroxidase Conjugate) was purchased from Kirkegaard and Perry Laboratories, Inc. as was the peroxidase-labelled Goat Anti-Rabbit IgG (H&L, human serum adsorbed).

Gelatin and antigen diluent buffer and the wash buffer for the first two washes consisted of 0.05M TrisHCl. 0.2M NaCl, pH 7.6,,with or without 10 μM EDTA (TSE buffer). The remaining wash solution and the antibody diluents came from the ELISAmate ® kit. The microtiter plates were scanned on a Titertek ® Multiscan plate reader at 405 nm.

Antigen sources:

Conditioned tissue culture media was obtained from human A2058 melanoma cell cultures. These cells were grown to 80% confluence in DMEM with fetal calf serum. The media was then discarded and replaced by serum-free DMEM. This media was harvested after 24 hours. It was centrifuged at 3600 rpm in a Sorvall ® RT 6000 for 10 min at 4° C. The supernatant was filtered through a 0.45 μ filter and concentrated to 10× by ultrafiltration using a YM 30 membrane (Amicon).

Purified enzymes:

Type IV procollagenase was purified from human A2058 melanoma cell conditioned media by gelatin affinity chromatography as described by Stetler-Stevenson et. al. (1989). The purified enzyme was stored at −70° C. until use. Samples of human rheumatoid synovial fibroblast collagenase and stromelysin were kindly provided by Dr. H. Nagase, Univ. of Kansas Medical Center.

Synthetic peptides:

The synthetic peptides used in the immunization procedures were made on a Biosearch 9600 peptide synthesizer using tBOC amino acid methodology.

Antibody source:

Antibodies were grown in New Zealand White rabbits using synthetic peptides coupled to bovine serum albumin with gluteraldehyde (0.14%). For the two initial immunizations, 1 mL of bovine serum albumin-peptide conjugate containing 0.2 mM equivalent of unconjugated peptide was mixed with 1 mL of complete Freund's adjuvant and emulsified prior to subcutaneous injection. For the remaining biweekly immunizations, 0.5 mL of bovine serum albumin-peptide conjugate was emulsified with 0.5 mL of complete Freund's adjuvant before injection.

Preparation of the peptide affinity column and affinity purification of the antipeptide antibodies:

Peptide affinity resins were prepared for both peptides using Affi-Gel 10 (BioRad) following the manufacturer's directions and using 2 mg of each peptide. These resins were used to affinity purify the antibodies from rabbit serum following heat treatment of the serum at 56° C. for 30 min. After absorption of the antibodies overnight, the columns were washed with 20 column volumes of cold phosphate buffered saline prior to elution with 2 bed volumes of 1M Acetic acid. This eluate was immediately neutralized by the addition of 6M NaOH followed by Diaflo buffer exchange using a YM 30 membrane (Amicon).

"Substrate Capture" Assay:

Gelatin was dissolved in the TSE buffer by warming to 55° C. in a water bath and allowed to cool to room temperature. 300 μL of this 1% gelatin solution was dispensed into the wells of the microtiter plate and allowed to incubate overnight at 37° C. The wells were emptied by inversion of the plate and the plate was chilled to 4° C. The wells were washed twice with TSE buffer and 150 μL of antigen (enzyme) solution was added to each well. Serial dilutions were made in TSE buffer. Antigen solutions were equilibrated for 1 hr at 4° C. with the substrate coating. The wells were then emptied by inversion and washed twice with TSE buffer. 150 μL of antipeptide antibody solution was then added. Antibody dilutions were made using the diluent/blocking solution from the ELISAmate ® kit. First antibody was incubated at 4° C. for 3 hr. The plate was then washed twice with wash solution. 150 μL of 0.5 μg/mL solution of goat anti-rabbit-peroxidase conjugate was added and incubated at 4° C. for 3 hr. The plate was washed twice before a final 5 min soak in wash solution. The plate was then emptied and color development reagents were added. Color development was allowed to proceed for 10 min before the plate was scanned at 405 nm on the Titertek ® Multiskan reader.

RESULTS

Figure 3A:
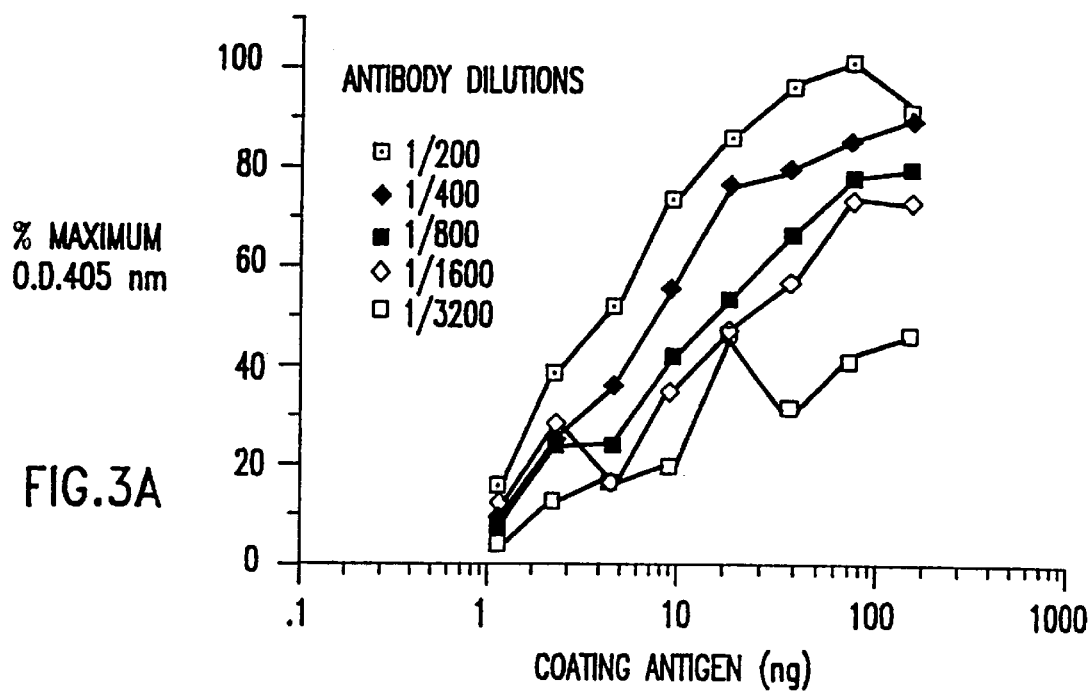
Figure 3B:
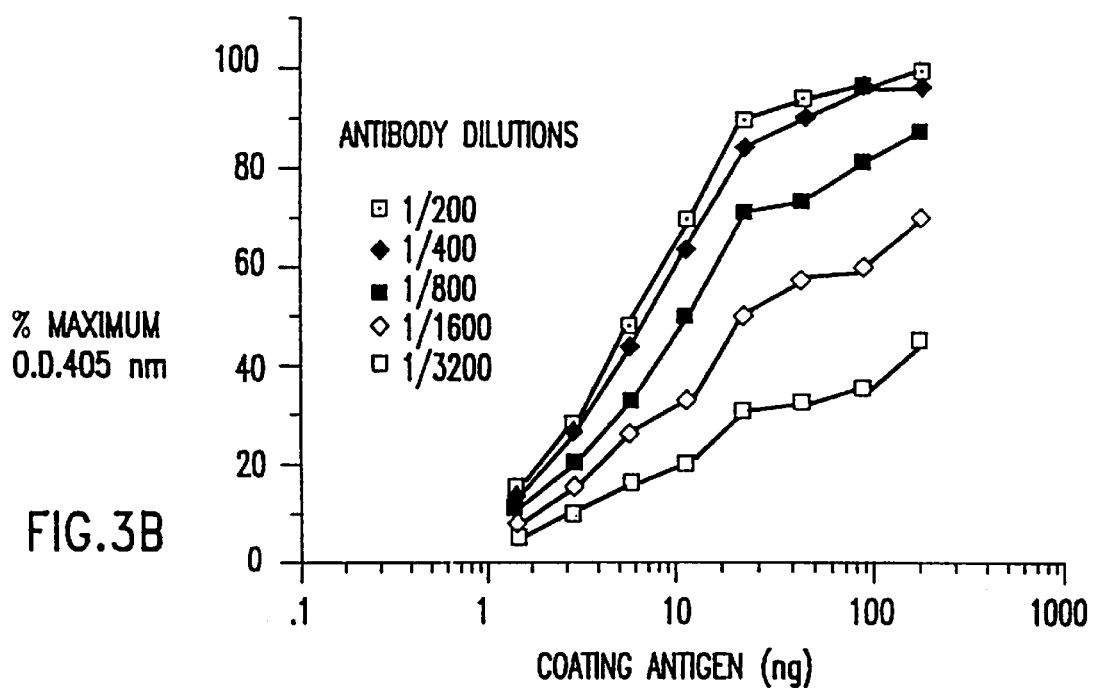
Figure 3C:
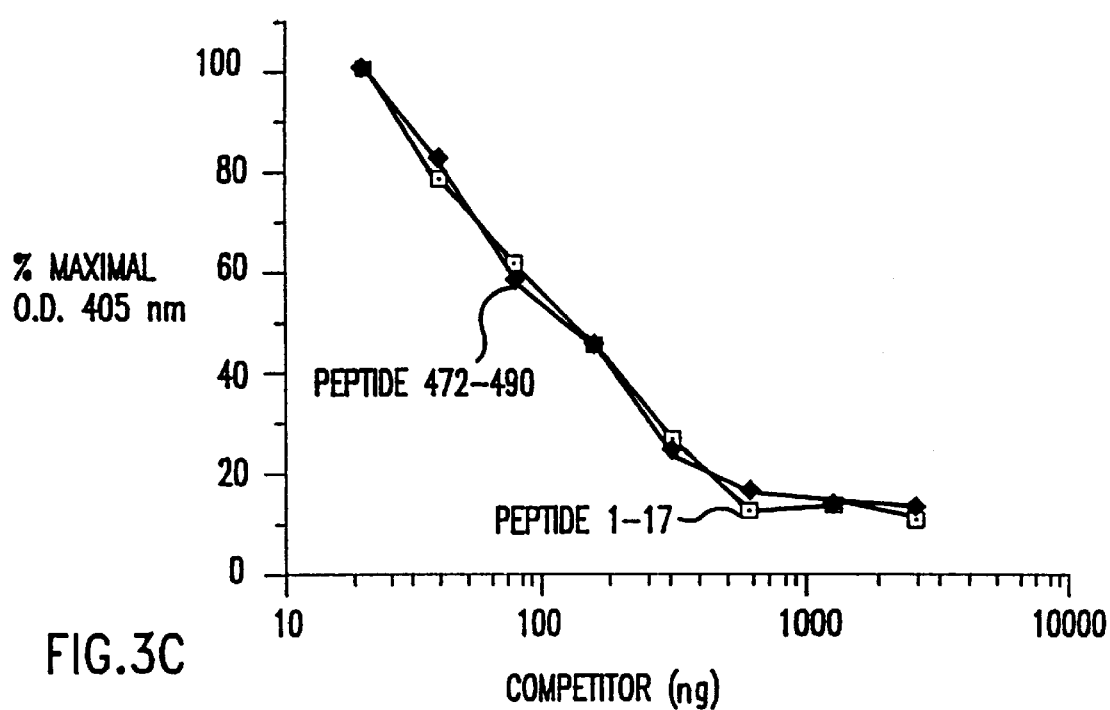

Affinity purified antipeptide antibodies were prepared against the amino terminal sequence of human melanoma cell type IV procollagenase as well as that of an internal domain beginning 159 residues from the carboxy terminus. These peptide sequences were chosen because they were obtained in the direct sequencing of the enzyme (Hohyta et. al., 1988; Collier et. al., and 1988), were confirmed in the predicted sequence from the cDNA clone (Collier et. al., 1988) and, as shown in FIG. 2, are derived from regions which do not show homology with other related metalloproteinases. The affinity purified antibodies were characterized using direct ELISA as well as in competition experiments, FIG. 3. The antibodies showed no cross reactivity with bovine serum or unrelated peptides.

The optimal concentrations of anti-type IV procollagenase antibodies and peroxidase-labelled conjugate antibody were obtained by checkerboard analysis using concentrated melanoma cell conditioned media as the source of enzyme. From this data an optimal dilution of 1/320 was chosen for the affinity purified antibody A1–17. Antibody A472–490 failed to show significant color development in this assay procedure. In attempting to reconcile this observation with the ability of this antibody A472–490 to detect the enzyme in immunoblot experiments we have concluded that the epitope for this antibody is not available in the native, soluble enzyme conformation. Conjugate antibody concentration was optimal at 0.5 $\mu$g/mL, and this concentration was used for the remainder of the experiments.

Figure 4A:
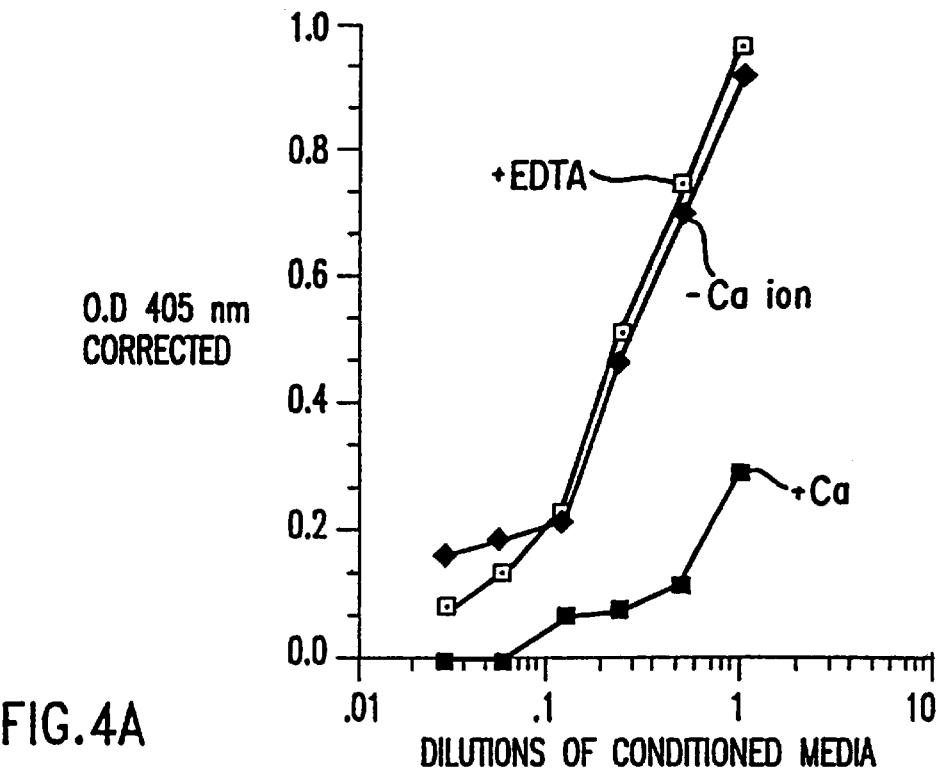
Figure 4B:
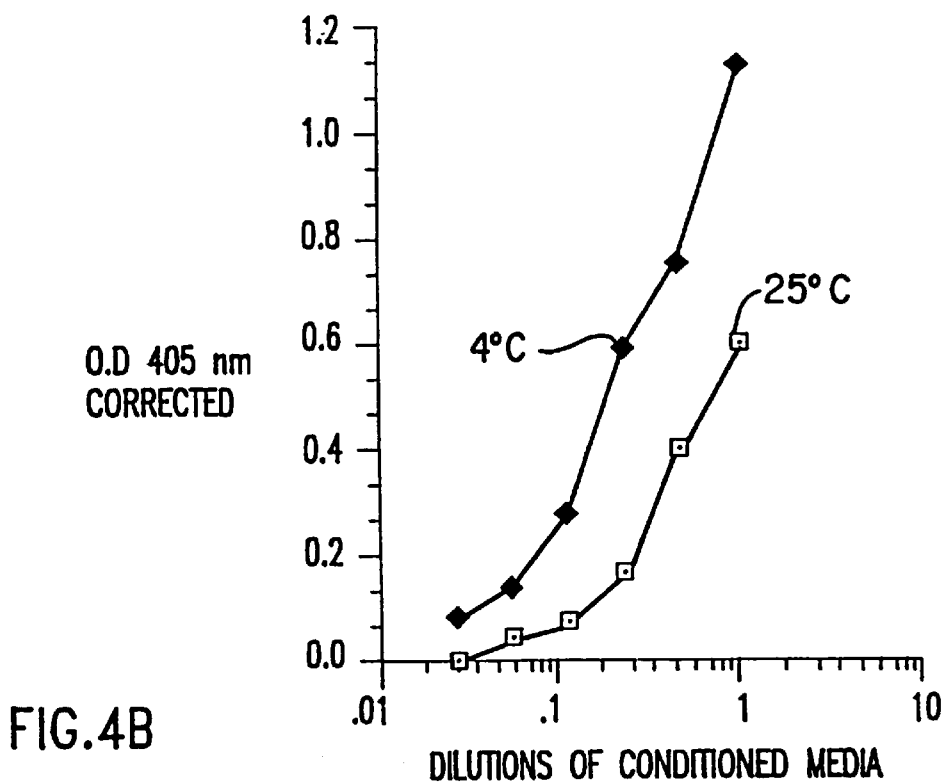

Type IV collagenase is a neutral metalloproteinase enzyme which requires calcium ion for enzyme activity (Liotta et. al., 1979; Liotta et.al., 1981). In order to investigate the possible effect of substrate degradation in this assay we tested the effect of excluding calcium ion and including in the buffer EDTA, an inhibitor of this and other neutral metalloproteinases (FIG. 4 A). Exclusion of calcium ion alone showed a significant increase in enzyme detection as assessed by total color development. Inclusion of a low concentration of EDTA (10 $\mu$M) allowed a slight improvement in the color development when compared to buffers with calcium exclusion alone. Temperature effects were also assessed. The optical density measurements were much higher, indicating a higher efficiency of enzyme capture, when the experiments were performed at 4° C. when compared with the results obtained at 25° C. (FIG. 4B).

Figure 5:
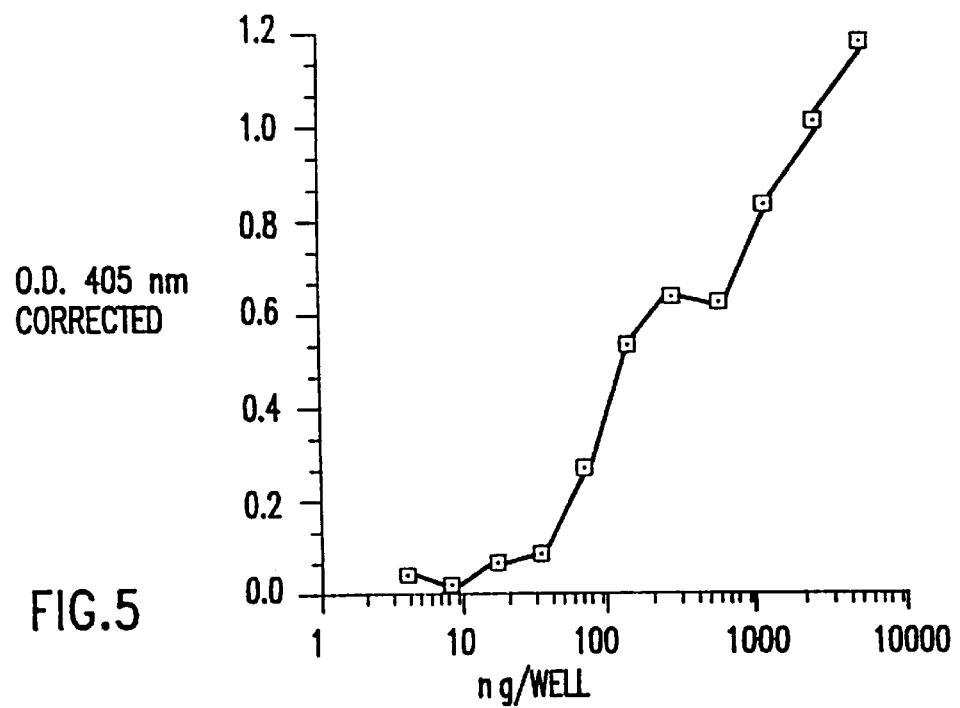
Figure 6:
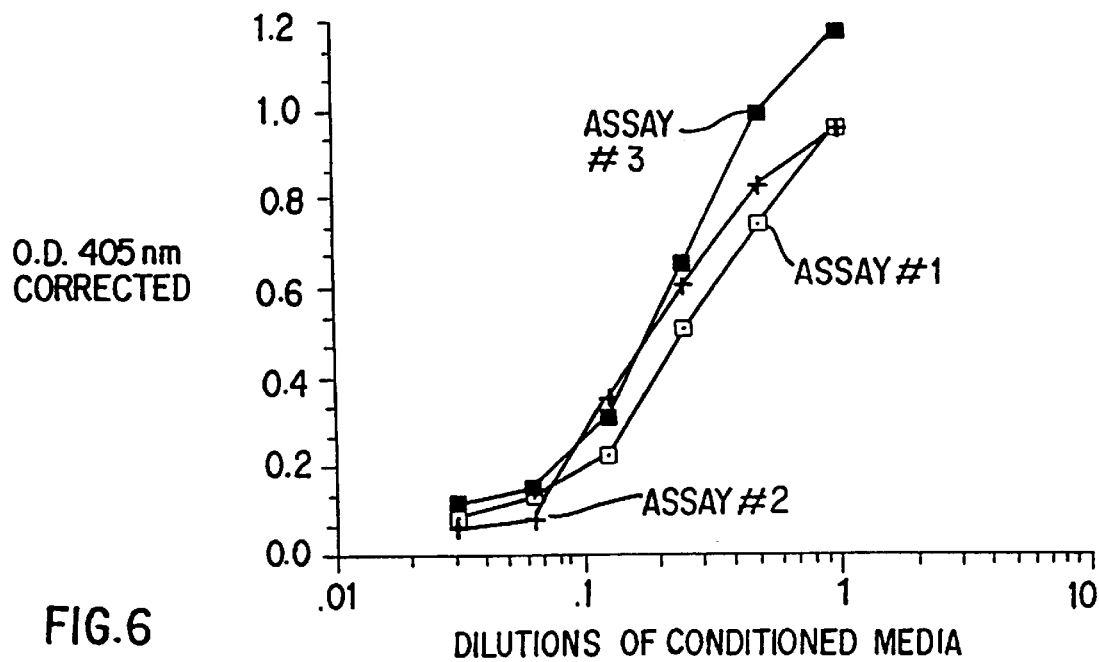
Figure 7:
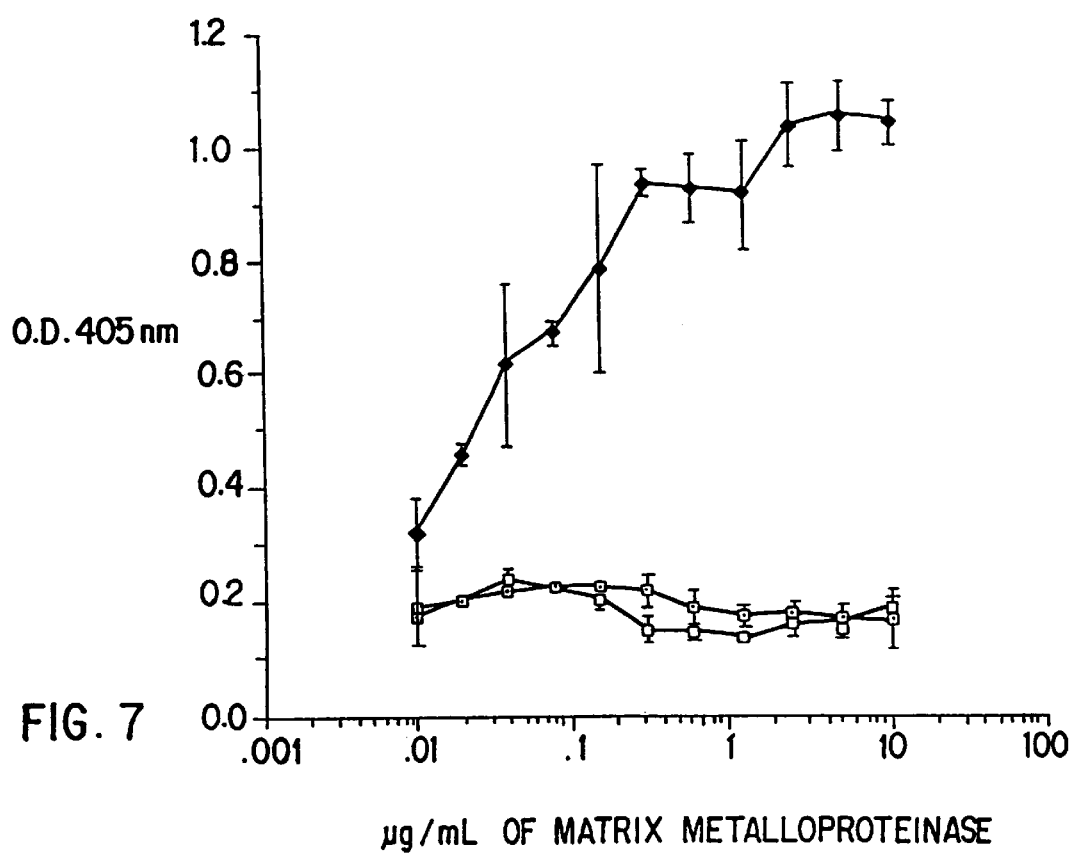

The sensitivity of the developed assay was tested using samples of highly purified type IV collagenase. Serial dilutions of 5 mg/mL stock solution of highly purified type IV collagenase were assayed using the substrate capture method. The results shown on FIG. 5 demonstrate that this method can detect as little as 50 ng of purified type IV collagenase corresponding to 0.3 ng/$\mu$L when the sample volume is restricted to 150 $\mu$L. The specificity of the assay was tested using samples of purified human rheumatoid synovial fibroblast collagenase and stromelysin. As shown in FIG. 6, these enzymes did not cross react with the type IV collagenase antibody in this system. Reproducibility of the assay was tested using conditioned media as a source of enzyme ( FIG. 7). These experiments allowed comparison of results from different sets of dilutions on the same plate or on different days. These results show that the assay is not only sensitive but highly reproducible.

We have designed and developed a reproducible, sensitive assay for quantitation of type IV collagenase. The assay principle is essentially that of a "sandwich" type assay except that the capture is achieved using an alternate substrate for this enzyme, gelatin. Gelatin coating of the ELISA plate wells allows adsorption of the type IV collagenase from solution. The immobilized enzyme is then detected by the addition of affinity purified antipeptide antibodies and goat anti-rabbit antibody-peroxidase conjugate.

This novel method uses a protease substrate to capture the antigen (enzyme). This method allows specific adsorption of the enzyme of interest as well as other gelatin binding proteins. This greatly simplifies the mixture in which the enzyme is detected and removes potentially interfering substances, thus avoiding some of the difficulties inherent in the usual assay protocol requiring coating of antigen or antibody directly onto the solid phase.

Enzyme detection is increased in the absence of calcium ion with or without addition of EDTA. Since the metalloproteinase activity requires the presence of calcium ions, these results suggest that the improved detection seen in the absence of calcium ion is due to inhibition of substrate (gelatin) degradation. As substrate degradation occurs the cleavage products and captured enzyme are washed from the plate, and consequently the color development is diminished. This substrate degradation effect is also observed in the study of temperature dependence of the assay, i.e. a lower color yield at higher assay temperatures.

The observation of the calcium ion dependent decrease in enzyme detection, further suggest that the gelatin binding domain of type IV collagenase is distinct from the active site, the former being calcium independent and the latter calcium dependent.

This method can detect type IV collagenase in conditioned media and will be useful for assessing the levels of enzyme secreted by different cell lines as well as the effects of various agents on enzyme secretion. Preliminary studies (data not shown) on human serum samples showed that this assay can detect type IV collagenase in samples from some patients with malignant lung cancers. This assay may prove useful in screening for particular cancers as well as clinical followup of patients who are being treated.

REFERENCES

Bonfil, R. D., Reddel, R. R., Ura, H., Reich, R., Fridman, R., Harris, C. C., and Klein-Szanto, A. J. P. (1989) Invasive and Metastatic Potential of v-Ha-ras-Transformed Human Bronchial Epithelial Cells. J. Natl. Cancer Inst. 81, 587.

Catt, K. and Treager, G. W. (1967) Solid-phase radioimmunoassay in antibody coated tubes. Science 158, 1570.

Collier, I. E., Wilhelm, S. M., Eisen, A. Z., Marmer, B. L., Grant, G. A., Seltzer, J. L., Kronberger, A., He, C., Bauer, E. A., Goldberg, G. I. (1988) H-ras Oncogene-transformed Human Bronchial Epithelial Cells (TBE-1) Secrete a Single Metalloproteinase Capable of Degrading Basement Membrane Collagen. J. Biol. Chem. 263, 6579

Engvall, E. and Perlmann, P. (1971) ELISA quantitative assay of immunoglobin G. Immunochemistry 8, 871.

Garbisa, S., Pozzatti, R., Muschel, R. J., Safflotti, U., Ballin, M., Goldfarb, R. H., Khoury, G., and Liotta, L. A. (1987) Secretion of Type IV Collagenolytic Protease and Metastatic Phenotype: Induction by Transfection with c-Ha-ras but not c-Ha-ras plus Ad2-E1a. Cancer Res. 47, 1523

Hohyta, M., Turpeenniemi-Hujanen, T., Stetler-Stevenson, W., Krutzsch, H., Tryggvason, K., and Liotta, L. A. (1988) Monoclonal Antibodies to type IV collagenase recognize a protein with limited sequence homology to interstitial collagenase and stromelysin. FEBS Lett. 233, 109.

Hudson, L. and Hay, F. C. (1980) Practical Immunology, 2nd edition, Blackwell Scientific Publications, Oxford, p. 237.

Leininger, R. I., Cooper, C. W., Falb, R. D. and Grode, G. A. (1966) Nonthrombogenic plastic surfaces. Science 152, 1625.

Liotta, L. A. (1980) Tumor Invasion and Metastasis- Role of the Extracellular Matrix: Rhoads Memroial Award Lecture. Cancer Res. 46, 1.

Liotta, L. A., Abe, S., Gehron-Robey, P., and Martin, G. R. (1979) Preferential digestion of basement membrane collagen by an enzyme derived from metstatic murine tumor. Proc. Natl. Acad. Sci. 76,2268.

Liotta, L. A., Tryggvason, K., Garbisa, S., Hart, I., Foltz, C. M., and Shafie, S. (1980)Metastatic potential correlates with enzymatic degredation of basement membrane collagen. Nature (London) 284, 67.

Liotta, L. A., Tryggvason, K., Garbisa, S., Gehron-Robey, P., and Abe, S. (1981) Partial Purification and Characterization of a Neutral Protease which Cleaves Type IV collagen. Biochemistry 20, 100.

Muschel, R., Williams, J. E., Lowy, D. R., and Liotta, L. A. (1985) Harvey-Ras Induction of Metastatic Potential Depends Upon Oncogene Activation and the Type of Recipient Cell. Am. J. Pathol. 121, 1.

Stetler-Stevenson, W. G., Krutszch, H. C., Wacher, M. P., Margulies, I. M. K., and Liotta, L. A. (1989) The Activation of Human Type IV Collagenase Proenzyme. Sequence Identification of the Major Conversion Product following Organomercurial Activation. J. Biol. Chem. 264, 1353.

Van Weeman, B. K. and Schorrs, A. H. W. M. (1971) Immunoassay using antigen enzyme conjugate. FEBS Lett. 15, 232.

We claim:

1. A method of detecting Type IV collagenase in a body fluid test sample comprising the steps of:

a) exposing a solid support having gelatin bound thereto to a body fluid test sample believed to contain Type IV collagenase;

b) exposing the product of step (a) to antibodies against Type IV collagenase;

c) exposing the product of step (b) to an antibody-peroxidase conjugate wherein the antibody of the conjugate is known to be reactive with the antibody which is bound to Type IV collagenase; and d) exposing the product of step (c) to a peroxidase color development reagent to determine the presence or absence of Type IV collagenase.

2. A method of quantitatively detecting Type IV collagenase in a body fluid comprising the steps of:

a) binding gelatin to solid substrates;

b) exposing the substrate of step (a) to varying amounts of Type IV collagenase or to test samples believed to contain Type IV collagenase;

c) exposing the product of step (b) to antibody which recognizes Type IV collagenase and allowing the antibody to bind to Type IV collagenase;

d) exposing the product of step (c) to antibody-peroxidase conjugates which will bind to the antibody which recognizes Type IV collagenase;

e) exposing the product from step (d) to a peroxidase development reagent; and f) comparing the response in test samples with substrates having known amounts of Type IV collagenase.

* * * * *